United States Patent [19]

Shih

[11] Patent Number: 5,633,250

[45] Date of Patent: May 27, 1997

[54] IMIDAZOYLALKYL SUBSTITUTED WITH A SIX OR SEVEN MEMBERED HETEROCYCLIC RING CONTAINING TWO NITROGEN ATOMS

[75] Inventor: Neng-Yang Shih, North Caldwell, N.J.

[73] Assignee: Schering Corporation, Kenilworth, N.J.

[21] Appl. No.: 460,825

[22] Filed: May 31, 1995

Related U.S. Application Data

[63] Continuation of Ser. No. 244,813, Jun. 10, 1994, which is a continuation-in-part of Ser. No. 810,642, Dec. 18, 1991, abandoned.

[51] Int. Cl.$^6$ .................. A61K 31/55; A61K 31/495; C07D 403/06
[52] U.S. Cl. .................. 514/218; 514/252; 544/229; 544/370; 544/384; 540/485; 540/487; 540/575; 548/341.1; 548/341.5; 548/343.1
[58] Field of Search .................. 540/575; 514/218

[56] References Cited

U.S. PATENT DOCUMENTS

| | | | |
|---|---|---|---|
| 3,491,098 | 1/1970 | Archer | 544/370 |
| 4,404,382 | 9/1983 | Gall | 544/360 |
| 4,404,438 | 9/1983 | Gall | 546/193 |
| 4,431,387 | 2/1984 | Wei et al. | 514/196 |
| 4,767,778 | 8/1988 | Arrang et al. | 514/397 |
| 4,935,417 | 6/1990 | Pascal et al. | 514/218 |
| 5,010,075 | 4/1991 | Pascal et al. | 514/218 |
| 5,071,859 | 12/1991 | Knudsen et al. | 514/326 |
| 5,091,428 | 2/1992 | Pascal et al. | 514/252 |
| 5,276,034 | 1/1994 | Pascal et al. | 540/575 |
| 5,342,960 | 8/1994 | Garbara et al. | 548/344 |
| 5,463,074 | 10/1995 | Shih et al. | 548/314.7 |

FOREIGN PATENT DOCUMENTS

| | | |
|---|---|---|
| 0289227 | 11/1988 | European Pat. Off. |
| 172383 | 7/1989 | Japan |
| 91/17146 | 11/1991 | WIPO |

OTHER PUBLICATIONS

West Jr. et al., Journal of Neurochemistry, vol. 55, No. 5, pp. 1612–1616 (1990).

West Jr. et al, Molecular Pharmacology, 38:610–613 (1990).

Korte et al., Biochemical and Biophysical Research Communications, vol. 168, No. 3, pp. 979–986 (1990).

Derwent Abstract 86–273706/42 for EP 0 197 840 (Oct. 1986).

Derwent Abstract 90–184730/24 for US 4 925 851 (May 1990).

Derwent Abstract 90–180087/24 for EP 372 125 (Jun. 1990).

Derwent Abstract 88–309195/44 for US 4 935 417 (Jun. 1990).

Appel, Current Neurology, vol. 6, pp. 289, 313–316, (1987) ("Alzheimer's Disease").

Schunack CA 80(15): 82801a (1973).

*Primary Examiner*—Emily Bernhardt
*Attorney, Agent, or Firm*—Henry C. Jeanette

[57] ABSTRACT

Disclosed us a compound of Formula 1.0:

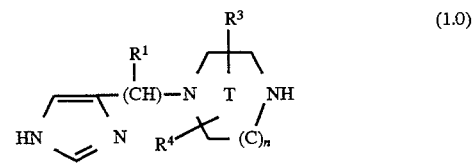

or a pharmaceutically acceptable salt or solvate thereof.

Also disclosed are pharmaceutical compositions comprising a pharmaceutically acceptable carrier and an effective amount of a Compound of Formula 1.0.

Further disclosed is a method of treating allergy (for example asthma), inflammation, hypertension, raised intraocular pressure (such as glaucoma)—i.e., a method of lowering intraocular pressure, sleeping disorders, states of hyper and hypo motility and acidic secretion of the gastrointestinal tract, hypo and hyperactivity of the central nervous system (for example, agitation and depression) and other CNS disorders (such as Alzheimers, Schizophrenia, and migraine) comprising administering an effective amount of a compound of Formula I to a patient in need of such treatment.

9 Claims, No Drawings

IMIDAZOYLALKYL SUBSTITUTED WITH A SIX OR SEVEN MEMBERED HETEROCYCLIC RING CONTAINING TWO NITROGEN ATOMS this is a continuation, of application Ser. No. 08/244,813, filed Jun. 10, 1994 which is the United States National Application corresponding to International Application No. PCT/US92/10697, filed Dec. 16, 1992, and designating the United States, which PCT Application is in turn a continuation-in-part of U.S. application Ser. No. 07/810642, filed Dec. 18, 1991 now abandoned, the benefit of which applications are claimed pursuant to the provisions of 35 U.S.C. 120, 363 and 365(C).

BACKGROUND $H_3$ receptor sites are known and are of current interest to those skilled in the art—for example, see: West, Jr. et al., "Biexponential Kinetics of (R)-α-[$^3$H]Methylhistamine Binding to the Rat Brain $H_3$ Histamine Receptor", Journal of Neurochemistry, Vol. 55, No. 5, pp. 1612–1616, 1990; West, Jr. et al., "Identification of Two $H_3$-Histamine Receptor Subtypes", Molecular Pharmacology, 38:610–613; and Korte et al., "Characterization and Tissue Distribution of $H_3$ Histamine Receptors in Guinea Pigs by $N^\alpha$-Methylhistamine", Biochemical and Biophysical Research Communications, Vol. 168, No. 3, pp. 979–986.

Arrang et al. in U.S. Pat. No 4,767,778 (Issued Aug. 30, 1988) disclose a pharmaceutical composition containing a histamine derivative of the formula:

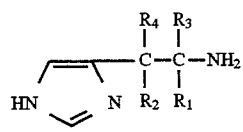

wherein each of $R_1$, $R_2$, and $R_4$, represents a hydrogen or a methyl, or $R_1$ and $R_2$ taken together represent a methylene, and $R_3$ is a hydrogen, a methyl or a carboxy, with the proviso that $R_1$, $R_2$, $R_3$, and $R_4$ are not simultaneously methyl groups. It is disclosed that the derivatives behave as complete agonists of the $H_3$ receptors in rat brain and produce a maximal inhibition of release identical to that induced by histamine (approximately 60%). It is also disclosed that the histamine derivatives powerfully inhibit the release and synthesis of histamine by very selectively stimulating the $H_3$ receptors. Consequently, according to Arrang et al., the derivatives are likely to decrease histaminergic transmission in the digestive tract and in the nervous, cardiovascular and immune systems. Arrang et al. disclose that the derivatives can be used in therapy as a drug having sedative effects, as a sleep regulator, anticonvulsant, regulator of hypothalamo-hypophyseal secretion, antidepressant, and modulator of cerebral circulation. According to Arrang et al., inhibition of the release of inflammation messengers in various allergic conditions (e.g., asthma) is expected to result from stimulation of the $H_3$ receptors of the lung. It is further disclosed that the inhibition of release of gastric histamine is likely to exert antisecretory and antiulcerative effects. According to Arrang et al., modification of release of the messengers of immune responses is likely to modulate the latter responses.

EP 0 338 939 discloses compounds of the formula:

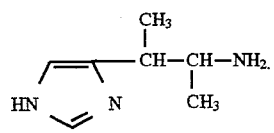

Derwent abstract 86-273706/42 for EP 0 197 840 discloses imidazole derivatives of the formula:

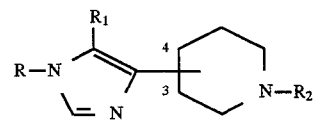

wherein $R_1$ is H, methyl or ethyl; R is H or $R_2$; and $R_2$ is 1–6C alkyl, piperonyl, 3-(benzimidazolon-1-yl)propyl, —CZ—$NHR_5$ or a group (i):

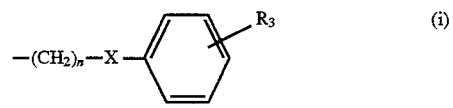

wherein n is 0–3; X is a bond, O, S, NH, CO, CH=CH or a group (ii):

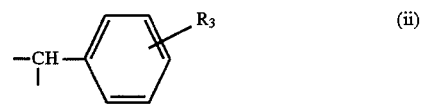

$R_3$ is H, methyl, halo, CN, $CF_3$ or $COR_4$; $R_4$ is 1–6C alkyl, 3–6C cycloalkyl or phenyl (optionally substituted by methyl or F); Z is O, S, NH, N-methyl or N—CN; and $R_5$ is 1–8C alkyl, 3–6C cycloalkyl (optionally substituted by phenyl), 3–6C cycloalkyl(1–3C)alkyl, phenyl (optionally substituted by methyl, halo or $CF_3$), phenyl(1–3C)alkyl, naphthyl, adamantyl or p-toluenesulphonyl. It is disclosed that these compounds are psychotropic agents. It is also disclosed that these compounds antagonise the histamine $H_3$ receptors and increase the speed of cerebral histamine renewal.

Derwent abstract 90-184730/24 for U.S. Pat. No. 4,925, 851 discloses 2- or 4-(2-(1H-imidazol-1-yl)ethyl) piperidine compounds useful as antitumour agents for inhibiting lymphoma, sarcoma, myeloma and leukaemia. The compounds have the formula:

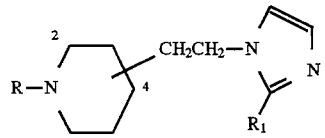

wherein R is —$CH_2(CH_2)_m$—Me, —CO—$(CH_2)_m$—Me or —CO—$CMe_2$—$R_2$; m is 2–18; $R_2$ is H or Me; $R_1$ is —$(CH_{2n}$—$R_3$; n is 0–13; $R_3$ is H, i—Pr or t—Bu; and the floating group is at the 2- or 4- position; with the proviso that (1) the sum of C atoms in $R_1$ does not exceed 13; and (2) the sum of C atoms in R and $R_1$ does not exceed 25.

Derwent abstract 90-180087/24 for EP 372125A discloses compounds of the formula:

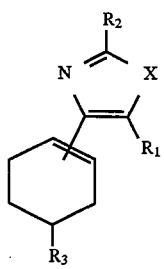

wherein X is O or S; $R_1$ is halo, $CF_3$, CN, $NO_2$, OH, or 1–6C alkoxy; $R_2$ is H, 1–6C alkyl, aryl, 7–13C aralkyl, optionally substituted amino or 5- or 6-membered N-containing ring; and $R_3$ is 1–6C hydrocarbyl, 7–13C aralkyl or 1–13C acyl. It is disclosed that these compounds have alpha2-antagonist activity with no dopamine activity and that they are useful for treating depression and other related illnesses (e.g., anxiety or cognitive disorders).

Derwent abstract 88-309195/44 for U.S. Pat. No. 4,935,417 discloses compounds of the formula:

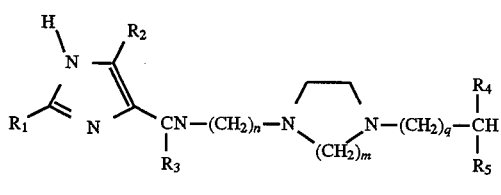

wherein (according to U.S. Pat. No. 4,935,417) $R^1$ is aryl, lower alkyl, cycloalkyl or hydrogen; $R^2$ is aryl, lower alkyl or hydrogen; $R^3$ is lower alkyl, hydroxy or hydrogen; $R_4$ is aryl or hydrogen; $R_5$ is aryl or hydrogen; m is two or three; n is zero, one or two, provided that when $R^3$ is hydroxy, n is one or two; and q is zero, one, two or three. U.S. Pat. No. 4,935,417 discloses that these compounds are calcium channel antagonists useful for treating mammals having a variety of disease states, such as stroke, epilepsy, hypertension, angina, migraine, arrhythmia, thrombosis, embolism and also for treatment of spinal injuries Compounds known in the art include:

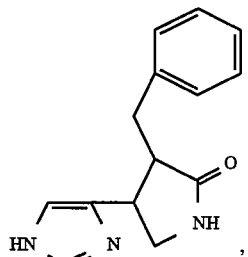

RN 85651-90-7
CA98(23):194919y

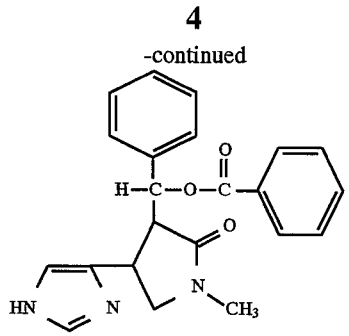

RN 81345-39-3
CA96(17):139642m and

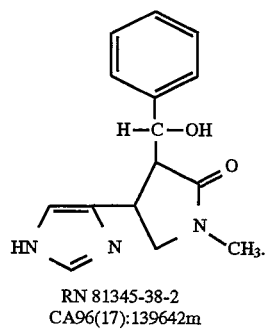

RN 81345-38-2
CA96(17):139642m

Known compounds in the art also include compounds of the formula:

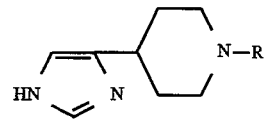

wherein R (Table 1) is:

TABLE 1

| NO. | R | RN | CA |
|---|---|---|---|
| 1 | —$CH_3$ | 106243-44-1 | 106(11):84602r |
| 2 | —$CH(CH_3)_2$ | 106243-45-2 | 106(11):84602r |
| 3 | H | 106243-23-6 | 106(11):84602r |
| 4 | —C(S)NHC($CH_3$)$_2$$CH_2$C($CH_3$) | 106243-93-0 | 106(11):84602r |
| 5 | —C(O)NHCH($CH_3$)(phenyl) | 106243-90-7 | — |
| 6 | —C(S)NH(p-chlorophenyl) | 106243-85-0 | — |
| 7 | —C(O)NH(phenyl) | 106243-77-0 | — |
| 8 | —C(NH)N($CH_3$)(cyclopropyl) | 106243-73-6 | — |
| 9 | —C(S)NH$CH_3$ | 106243-61-2 | — |
| 10 | —$CH_2CH_2$-phenyl | 106243-49-6 | — |
| 11 | —$CH_2CH_2$-p-flurophenyl | 106243-67-8 | — |
| 12 | benzyl | 106243-25-8 | — |

Additionally known compounds include:

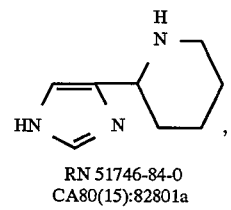

RN 51746-84-0
CA80(15):82801a

-continued (2) 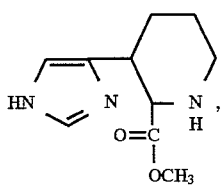

RN 67319-35-1
CA89(13):109229v (3) 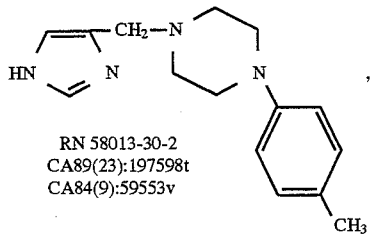

RN 58013-30-2
CA89(23):197598t
CA84(9):59553v (4) 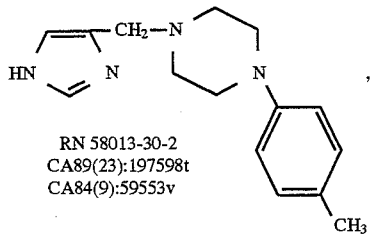

RN 58013-29-9
CA89(23):197598t
CA84(9):59553v (5) 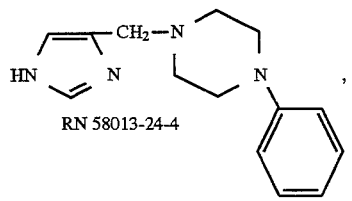

RN 58013-24-4

(6) 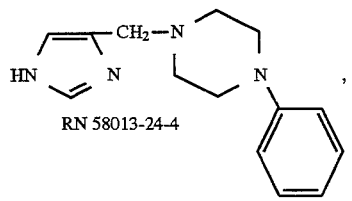

RN 18505-67-4
CA72(17):90459v
CA69(3):10467w (7) 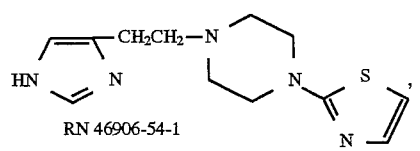

RN 46906-54-1

(8) 

RN 46995-90-8 and (9) 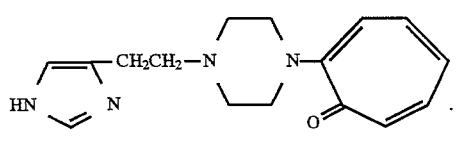

RN 80101-09-3
CA96(1):6760b

In view of the art's interest in compounds which effect the H₃ receptors, novel compounds having agonist or antagonist activity on H₃ receptors would be a welcome contribution to the art. This invention provides just such a contribution by providing novel compounds having H₃ agonist or antagonist activity.

SUMMARY OF THE INVENTION

This invention provides compounds of the formula:

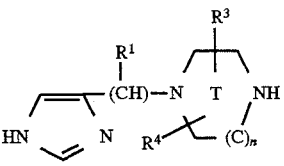
(1.0)

or a pharmaceutically acceptable salt or solvate thereof, wherein:

(A) n is 1 or 2, such that when n is 1 then ring T is a six membered ring, and when n is 2 then ring T is a seven membered ring;

(B) $R^1$ is selected from the group consisting of:
  (1) H;
  (2) $C_1$ to $C_6$ alkyl;
  (3) allyl; and
  (4) propargyl;

(C) $R^3$ and $R^4$ are independently selected from the group consisting of:
  (1) H;
  (2) $C_1$ to $C_6$ alkyl;
  (3) allyl;
  (4) propargyl; and
  (5) —$(CH_2)_q$—$R^5$ wherein q is an integer of: 1 to 7, and $R^5$ is selected from the group consisting of: phenyl, substituted phenyl, —$OR^6$, —$C(O)OR^6$, —$C(O)R^6$, —$OC(O)R^6$, —$C(O)NR^6R^7$, CN and —$SR^6$ wherein $R^6$ and $R^7$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains from 1 to 3 substituents;

(D) $R^6$ and $R^7$ are each independently selected from the group consisting of: H and $C_1$ to $C_6$ alkyl; and (E) $R^3$ and $R^4$ are each independently bound to the same or different carbon atom of ring T.

Those skilled in the art will appreciate that the total number of substituents on each —$(C_n)$—is two, and that such substituents are independently selected from the group consisting of H, $R_3$, and $R_4$, such that there is only one $R^3$ and one $R^4$ substituent in ring T.

This invention also provides pharmaceutical compositions comprising a pharmaceutically acceptable carrier and an effective amount of a Compound of Formula 1.0.

This invention further provides a method of treating allergy, (for example asthma), inflammation, hypertension, raised intraocular pressure (such as glaucoma)—i.e., a method of lowering intraocular pressure, sleeping disorders (e.g., hypersomnia, somnolence, narcolepsy and sleeplessness, such as insomnia), states of hyper and hypo motility and acidic secretion of the gastrointestinal tract, hypo and hyperactivity of the central nervous system (for example, agitation and depression) and other CNS disorders (such as Alzheimers, Schizophrenia, and migraine) comprising administering an effective amount of a compound of Formula I to a patient in need of such treatment.

DETAILED DESCRIPTION OF THE INVENTION

As used herein the following terms have the following meanings unless indicated otherwise:

alkyl—represents a straight or branched, saturated hydrocarbon chain having from 1 to 6 carbon atoms;

cycloalkyl—represents a saturated carbocyclic ring having from 3 to 6 carbon atoms;

halogen (halo)—represents fluoro, chloro, bromo or iodo;

DMF—stands for N,N,-dimethylformamide;

SEM—stands for 2-(trimethylsilyl)ethoxymethyl; and

THF—stands for tetrahydrofuran.

Also, unless stated otherwise, the substituents for the various embodiments described below are as defined for Formula 1.0.

In the compounds of this invention, preferably $R^3$ and $R_4$ are each independently selected from the group consisting of: H, $C_1$ to $C_6$ alkyl, allyl, propargyl, and $-(CH_2)_q-R_5$ wherein $R^5$ is phenyl or substituted phenyl. Most preferably, $R^1$, $R_3$ and $R^4$ are each independently selected from the group consisting of H and $C_1$ to $C_6$ alkyl. More preferably, $R^1$, $R^3$ and $R^4$ are each independently selected from H and methyl. Preferably, $R^1$, $R^3$ and $R^4$ are H.

Representative compounds of this invention include compounds of the formula:

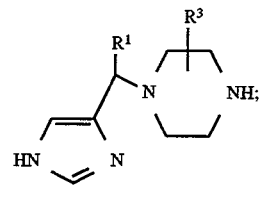

(2.0)

and

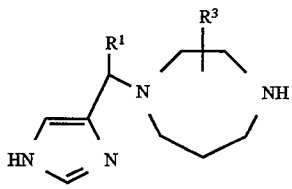

(4.0)

Representative compounds of Formula 1.0 include:

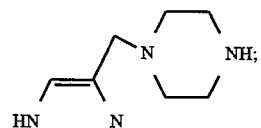

(2.1)

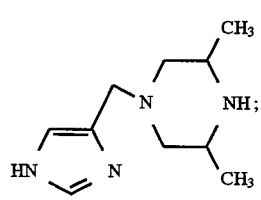

(2.2)

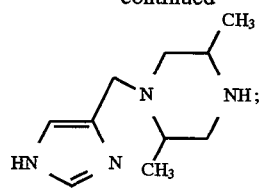

(2.3)

and

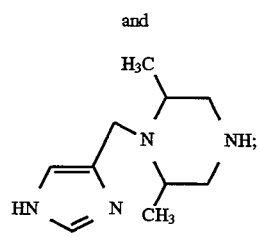

(2.4)

Representative compounds of Formula 1.0 also include:

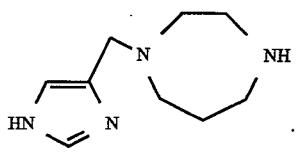

(4.1)

Certain compounds of the invention may exist in different isomeric (e.g., enantiomers and diastereoisomers) forms. The invention contemplates all such isomers both in pure form and in admixture, including racemic mixtures. Enol forms are also included.

The compounds of Formula 1.0 can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Certain basic compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The following processes may be employed to produce compounds of Formula 1.0. Unless stated otherwise, reactions are conducted at an appropriate temperature which allows the reaction to proceed at a reasonable rate to completion.

A. PREPARATION OF COMPOUND, WHEREIN m IS 1

SCHEME 1

In Step 1 of Scheme 1, compound (1), wherein n is 1 or 2, is reacted with compound (2) at a temperature of about 20° to about 80° C. in an organic solvent to produce compound (3). Preferably, ethanol is used as the organic solvent, but other suitable solvents include methanol, propyl alcohol and the like.

In Step 2 of Scheme 1, compound (3) is then dissolved in an aqueous acid to form a salt, compound (4). Examples of aqueous acids include HCl, HBr, $H_2SO_4$ and the like. Preferably HCl is employed (i.e., in compound (4) HA is HCl). The above reaction is conducted at a temperature of about −20° to about 20° C. Alternatively, compound (3) is reacted with di-t-butyl-dicarbonate in an organic solvent (e.g., DMF, $CH_2Cl_2$ and the like) at a temperature of about 0° to about 50° C., and the reaction product (compound (3) wherein the NH groups of the imidazole and the cyclic amine are protected with —C(O)O(t-butyl)) is then reacted with aqueous acid at a temperature of about −20° to about 20° C. to produce compound (4).

Compound (2) is prepared is three steps from Compound Z represents the protecting group:

Z can be other groups, such as 2-(trimethylsilyl)ethoxymethyl, benzyloxycarbonyl and the like; however, unless stated otherwise, Z preferably represents the trityl group in the processes as described below for making the compounds of this invention.

Those skilled in the art will appreciate that other protecting groups known in the art may be used-such as, for example, base sensitive groups wherein the protected compounds would be deprotected using basic conditions (e.g., NaOH). The processes described herein wherein the protected compound is deprotected under acidic conditions may also be carried out under basic conditions when a base sensitive protecting group is used.

Compound (5) is reacted with an organometallic reagent $R^1M$, wherein M is Li or MgBr, to produce compound (6). The reaction takes place in an inert organic solvent at a temperature of about −78° to 0° C. Suitable inert organic solvents include: THF, diethyl ether and the like. Compound (6) is then reacted with thionyl chloride in an inert organic solvent such as benzene or $CH_2Cl_2$, in the presence of base to generate compound (7). The reaction is conducted at a temperature of about −20° to 80° C. Suitable bases include: pyridine, triethylamine and the like. Preferably, triethylamine is used as the amine base. Compound (7) is then deprotected with dilute aqueous acid, such as HCl or HBr, at a temperature of about 50° to about 90° C. to produce compound (2). Other protecting groups are removed by methods known in the art. Compound (5) can be obtained by following the literature procedure set forth in J. K. Kelly, et al., J. Med. Chem. 20, 721(1977).

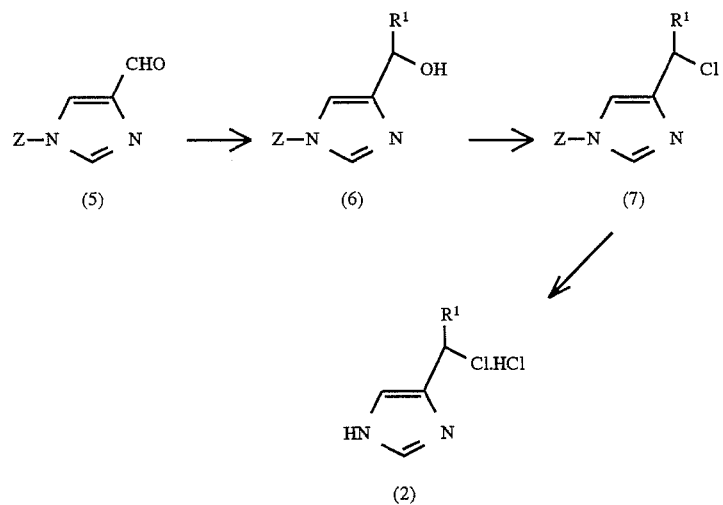

B. PREPARTION OF COMPOUNDS WHEREIN m IS 1

SCHEME 2

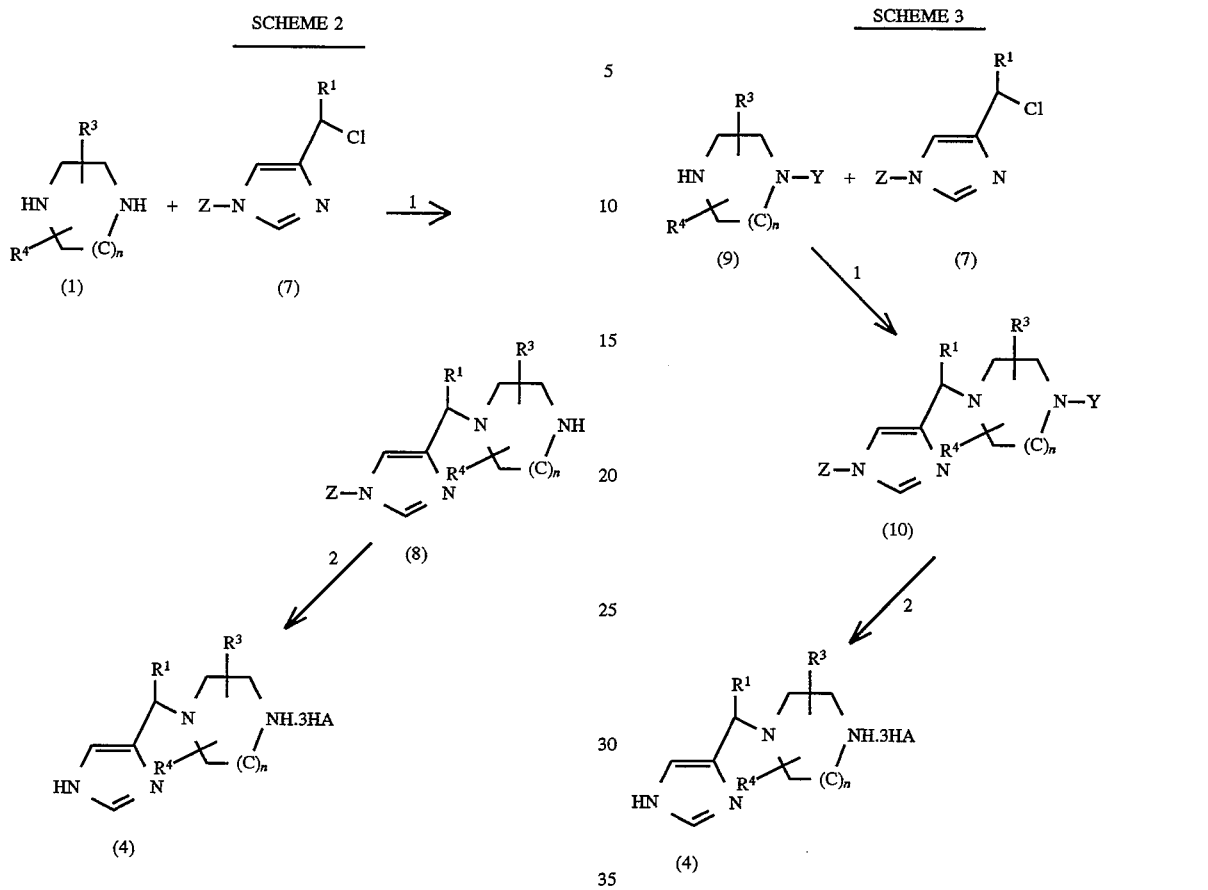

In Step 1 of Scheme 2, compound (8) is produced by reacting compound (1) with compound (7) in an inert organic solvent at a temperature of about 20° to about 80° C. Suitable organic solvents include THF, DMF, ethanol and the like. Preferably THF is used as the organic solvent. The reaction can be conducted with or without amine base. Suitable bases include triethylamine and the like. Compound (8) is then deprotected with dilute aqueous acid (HA) at a temperature of about 50° to about 90° C. to generate compound (4). Suitable aqueous acids include HCl, HBr, and the like.

C. PREPARATION OF COMPOUNDS WHEREIN m IS 1

SCHEME 3

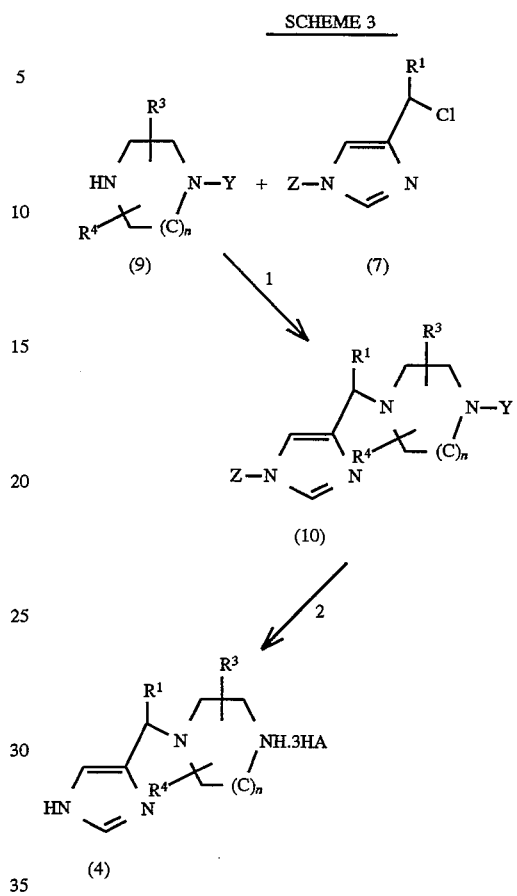

By following the steps in Scheme 2, with the exception that compound (9) (wherein n is 1 or 2, and Y is a protecting group such as trityl, $-C_2C(CH_3)_3$, or SEM group) is used instead of compound (1), compound (4) is produced.

D. PREPARATION OF COMPOUNDS WHEREIN m IS 1

SCHEME 4

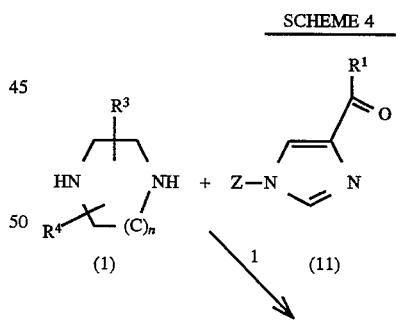

-continued
SCHEME 4

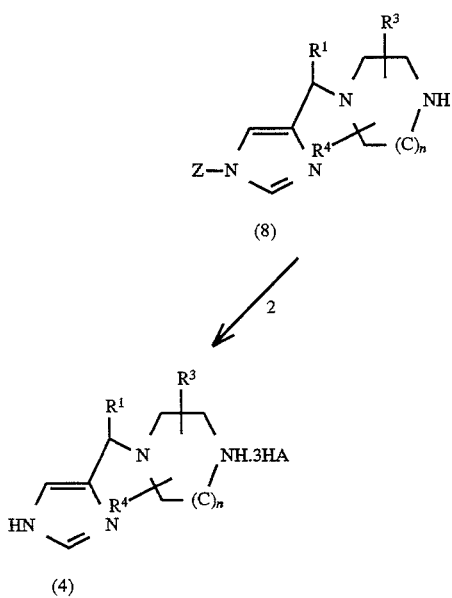

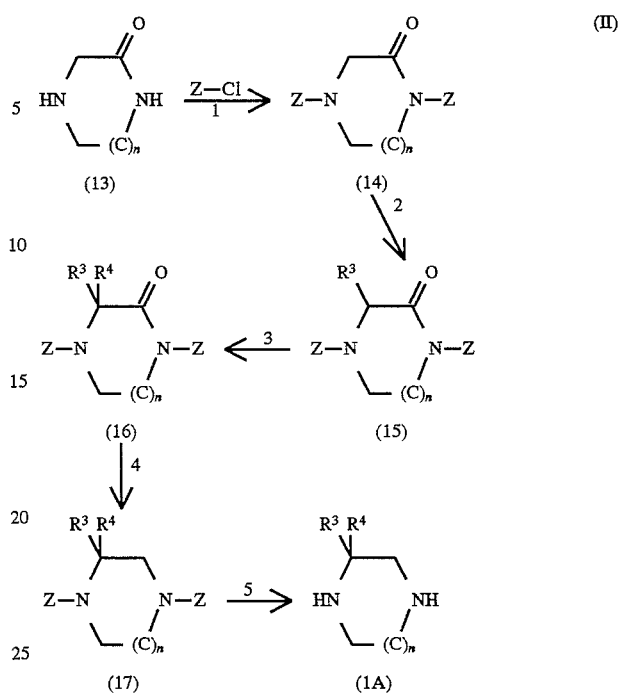

In Step 1 of Scheme 4, compound (11) is reacted with compound (1), in an inert organic solvent and in the presence of a reducing agent, to produce compound (8). The reaction can be conducted at a temperature of about −20° to about 50° C. Methanol is the preferred organic solvent; however, other suitable solvents include ethanol, DMF and the like. Suitable reducing agents include $NaBH_3CN$, $NaBH_4$, and Pd/C. When the latter (Pd/C) is employed as the reducing agent, the reaction is conducted under $H_2$ atmosphere. The conversion of compound (8) to compound (4) is accomplished by following the same procedure described above in Step 2 of Scheme 2.

Compound (1)

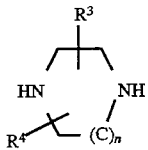

may be prepared by:

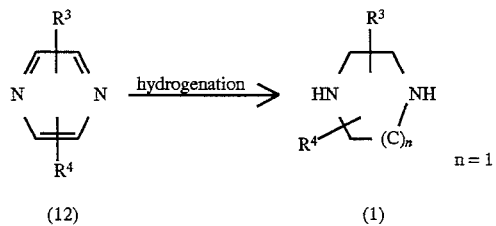

The hydrogenation of compound (12) is carried out using Pd-black as the catalyst, in an organic solvent, e.g., ethanol, methanol, THF and the like, using a temperature of about 20° to about 100° C., under a hydrogen at a pressure of about 1 to about 10 atmospheres.

In Step (1) of (II), compound (13) is reacted with Z—Cl in an organic solvent in the presence of a base to produce compound (14), The reaction is carried out at a temperature of about 0° to about 70° C. Examples of suitable bases include NaH, KH and the like. Suitable solvents include THF, DMF and the like. Z represents trityl or $(CH_3)_3CSi(CH_3)_2$—.

In Step (2) of (II), the anion of compound (14) is reacted with $R_3$—L in an organic solvent to produce compound (15). The reaction is carried out at a temperature of about −78° to about 50° C. Examples of solvents include THF, 1,4-dioxane and the like. L represents a leaving group, such as, for example, Cl, Br, I and the like. The anion of compound (14) is generated by reacting compound (14) with a base, such as LDA, KH and the like.

In Step (3) of (II), the anion of compound (15) is reacted with $R^4$—L in an organic solvent to produce compound (16). The reaction is carried out at a temperature of about −78° to about 50° C. Examples of solvents include THF, 1,4-dioxane and the like. L represents a leaving group, such as, for example, Cl, Br, I and the like. The anion of compound (15) is generated by reacting compound (15) with a base, such as LDA, KH and the like.

In Step (4) of (II), compound (16) is reduced with $LiAlH_4$ to produce compound (17). The reduction takes place in an organic solvent, such as THF, 1,4-dioxane and the like, and at a temperature of about 20° to about 100° C.

In Step (5) of (II), compound (17) is deprotected, to produce compound (1A), using aqueous acid, such as HCl, HBr, HI and the like. The deprotection step is carried out at a temperature of about 25° to about 100° C. in an organic solvent, such as 1,2-dichloroethane, ethanol and the like.

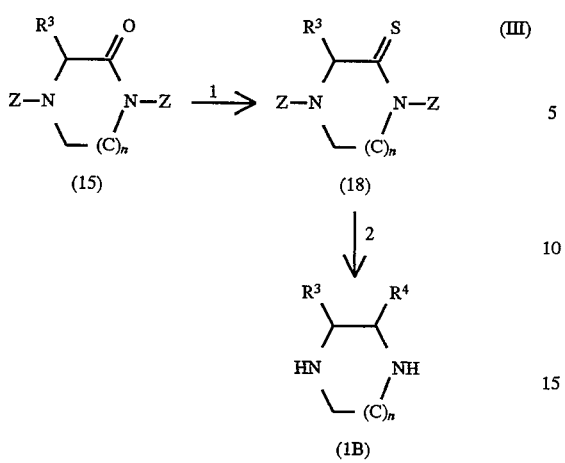

In Step (1) of (III), compound (15) is reacted with lawesson's reagent to produce compound (18). The reaction is carried out at a temperature of about 50° to about 120° C. in an organic solvent, such as toluene, benzene and the like.

In Step (2) of (III), compound (18) is reacted with $R^4M$, wherein M represents Li or the grignard reagent MgX (X represents halogen), which is then followed by reaction with $LiAlH_4$ to produce compound (1). A similar reaction is described in Tet. Letters, 28, 1529 (87).

In the above processes, it is sometimes desirable and/or necessary to protect certain groups during the reactions. Certain protecting groups are employed in the above processes but, as those skilled in the art will recognize, other protecting groups may be used in their place. Conventional protecting groups are operable as described in Greene, T. W., and Wuts, P. G. M., "Protective Groups In Organic Synthesis," John Wiley & Sons, New York, 1991; the disclosure of which is incorporated herein by reference thereto. After the reaction or reactions, the protecting groups may be removed by standard procedures.

The compounds of this invention are either agonists or antagonists of the histamine $H_3$ receptor. The binding affinity of the compounds of the invention to the $H_3$ receptor may be demonstrated by the procedure described below:

$H_3$ Receptor Binding Assay

The source of the $H_3$ receptors in this experiment was guinea pig brain. The animals used weighed 400–600 g. The tissue was homogenized using a Polytron in a solution of 50 mM Tris, pH 7.5. The final concentration of tissue in the homogenization buffer was 10% w/v. The homogenates were centrifuged at 1000×g for 10 min. in order to remove clumps of tissue and debris. The resulting supernatants were then centrifuged at 50,000×g for 20 min. in order to sediment the membranes, which were next washed 3 times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/mL with 0.1% DMSO. Membranes were then added (400 μg of protein) to the reaction tubes. The reaction was started by the addition of 3 nM [$^3$H]R-α-methylhistamine (8.8 Ci/mmol) or [$^3$H]-N-methylhistamine (80 Ci/mmol) and incubated at 30° for 30 min. Bound ligand was separated from unbound ligand by filtration, and the amount of radioactive ligand bound to the membranes was quantitiated by liquid scintillation spectrometry. All incubations were performed in duplicate and the standard error was less than 10% in all instances. Compounds that inhibited greater than 70% of the specific binding of radioactive ligand to the receptor were serially diluted to determine a $K_i$ (μM). The results are given in Table 2.

In Table 2, the compound represented by (a*) is known in the art.

TABLE 2

| COMPOUND | $H_3$ Binding $K_i$(μM) |
|---|---|
| (a*) HN–N=/–CH=/–CH₂NH₂·2HCl | 0.014 |
| HN–N=/–CH=/–CH₂–N(piperazine)NH·3HCl | 0.0047 |
| HN–N=/–CH=/–CH(NH₃C)–N(piperazine-CH₃)NH·3HCl | 6% |
| HN–N=/–CH=/–CH(CH₃)–N(piperazine-CH₃)NH·3HCl | 24% |
| HN–N=/–CH=/–CH₂–N(homopiperazine)NH·3HCl | 0.087 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 1 mg to 2000 mg/day preferably 10 to 1000 mg/day, in one to four divided doses to achieve relief of the symptoms. The compounds are non-toxic when administered within this dosage range.

The invention disclosed herein is exemplified by the following examples, which should not be construed to limit the scope of the disclosure. Alternative mechanistic pathways and analogous structures within the scope of the invention may be apparent to those skilled in the art.

To a refluxing solution of 8.6 g of piperidine in 50 mL of absolute ethanol was added a solution of 1.53 g of 4-chloromethylimidazole hydrochloride (1) in 10 mL of absolute ethanol for over 1.5 hr. After an additional 2 hours of refluxing, the reaction mixture was cooled and the ethanol and excess piperidine were removed by vacuum distillation. The residue (2) was used directly in Step B (below).

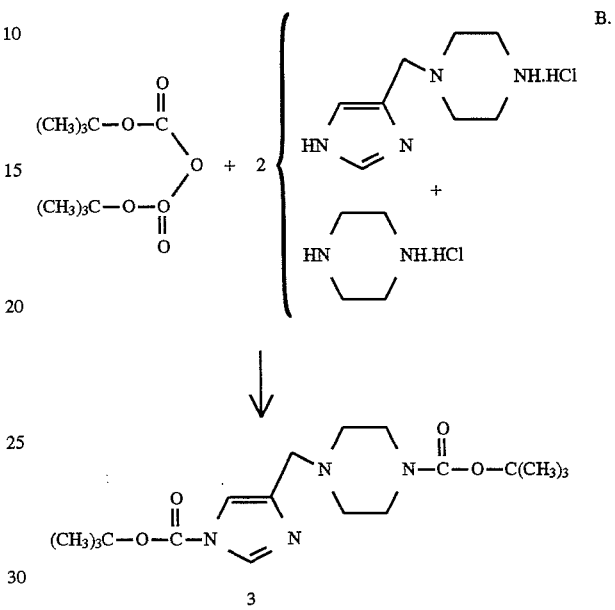

To a mixture of the residue 2 in 70 mL of anhydrous DMF was added 19 mL of triethylamine and 21 mL of di-t-butyldicarbonate at room temperature under nitrogen. The resulting mixture was stirred for 29 hours, and then it was filtered. The filtrate was concentrated under vacuum and the residue was purified by flash chromatography on silica gel to give 1.73 g of the compound of formula 3 (50% yield from 1), which was recrystallized in ethyl acetate. MS (FAB) 367 (M+1).

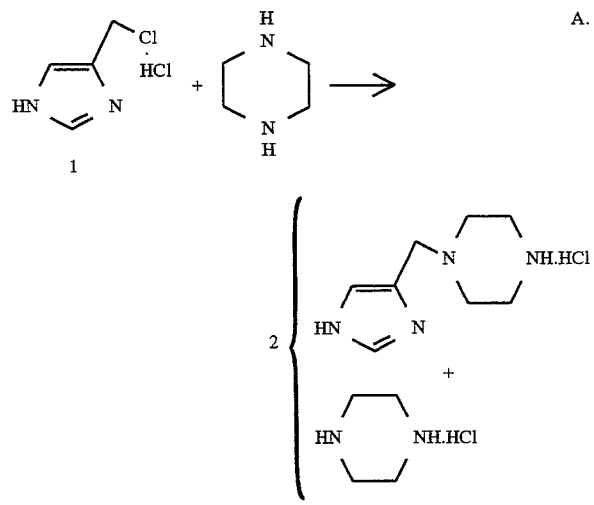

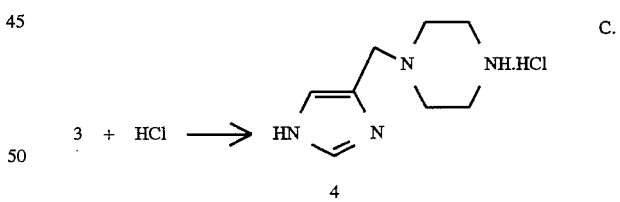

A stirring solution of 1.2 g of compound of formula 3 in 20 mL of ethyl acetate was cooled to 0° C., and dry HCl gas was bubbled in for 1 hour. The solid precipitate that resulted was filtered and recrystallized in methanol to give 0.75 g of the compound of formula 4 (80% yield). MS (EI) 166 ($M^+$).

Following the procedure described above in Steps A to C of Example 1, and using the starting compounds set forth in Table 3, compounds 5 to 7 were prepared.

TABLE 3

| STARTING COMPOUND | PRODUCT | MS (m/z) |
|---|---|---|
| (structure) HN–NH (7-membered ring) | (structure) 5 | (EI) 180 (M+) |
| (structure) HN–NH with two CH₃ | (structure) 6 | (CI) 195 (M+) |
| (structure) HN–NH with two CH₃ | (structure) | (CI) 195 (M+) |

The following are examples of pharmaceutical dosage forms which contain a compound of the invention. As used therein, the term "active compound" is used to designate the compound

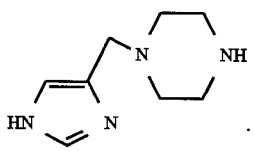

The scope of the invention in its pharmaceutical composition aspect is not to be limited by the examples provided, since any other compound of structural formula 1.0 can be substituted into the pharmaceutical composition examples.

Pharmaceutical Dosage Form Examples

EXAMPLE A

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

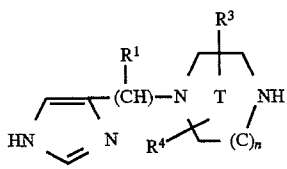 (1.0)

or a pharmaceutically acceptable salt or solvate thereof, wherein:

(A) n is 2, such that ring T is a seven membered ring;
(B) $R^1$ is selected from the group consisting of:
  (1) H;
  (2) $C_1$ to $C_6$ alkyl;
  (3) allyl; and
  (4) propargyl;
(C) $R^3$ and $R^4$ are independently selected from the group consisting of:
  (1) H;
  (2) $C_1$ to $C_6$ alkyl;
  (3) allyl;
  (4) propargyl; and
  (5) —$(CH_2)_q$—$R^5$ wherein q is an integer of: 1 to 7, and $R^5$ is selected from the group consisting of: phenyl, substituted phenyl, —$OR^6$, —$C(O)OR^6$, —$C(O)R^6$, —$OC(O)R^6$, —$C(O)NR^6R^7$, CN and —$SR^6$ wherein $R^6$ and $R^7$ are as defined below, and wherein the substituents on said substituted phenyl are each independently selected from the group consisting of: —OH, —, O—($C_1$ to $C_6$)alkyl, halogen, $C_1$ to $C_6$ alkyl, —$CF_3$, —CN, and —$NO_2$, and wherein said substituted phenyl contains from 1 to 3 substituents;
(D) $R^6$ and $R^7$ are each independently selected from the group consisting of: H and $C_1$ to $C_6$ alkyl; and
(E) $R^3$ and $R^4$ are each independently bound to the same or different carbon atom of ring T.

2. The compound of claim 1 wherein $R^3$ and $R_4$ are each independently selected from the group consisting of: H, $C_1$ to $C_6$ alkyl, allyl, propargyl, and —$(CH_2)_q$—$R^5$ wherein $R^5$ is phenyl or substituted phenyl.

3. The compound of claim 1 wherein $R^1$, $R^3$ and $R^4$ are each independently selected from the group consisting of H and $C_1$ to $C_6$ alkyl.

4. The compound of claim 3 wherein $R^1$, $R^3$ and $R^4$ are each independently selected from H and methyl.

5. The compound of claim 1 wherein said compound is selected from the group consisting of compounds having the formula:

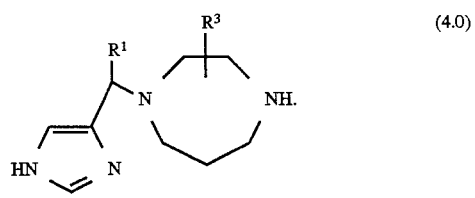 (4.0)

wherein $R^1$ and $R^3$ are as defined in claim 1.

6. The compound of claim 5 wherein $R^1$ and $R^3$ are each independently selected from the group consisting essentially of: H, and $C_1$ to $C_6$ alkyl.

7. The compound of claim 6 wherein $R^1$ and $R^3$ are each independently selected from H and methyl.

8. A compound having the formula:

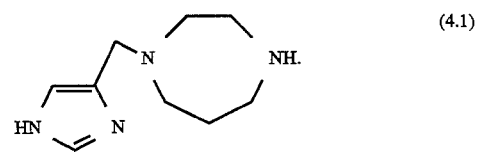 (4.1)

9. A pharmaceutical composition comprising a pharmaceutically acceptable carrier and an effective amount of a Compound of claim 1.

* * * * *